(12) United States Patent
Litvak et al.

(10) Patent No.: US 9,232,321 B2
(45) Date of Patent: Jan. 5, 2016

(54) SYSTEMS AND METHODS FOR IMPROVING REPRESENTATION BY AN AUDITORY PROSTHESIS SYSTEM OF AUDIO SIGNALS HAVING INTERMEDIATE SOUND LEVELS

(75) Inventors: Leonid M. Litvak, Los Angeles, CA (US); Nobutaka Okuyama, Valencia, CA (US); Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 181 days.

(21) Appl. No.: 14/114,908

(22) PCT Filed: May 26, 2011

(86) PCT No.: PCT/US2011/038169
§ 371 (c)(1),
(2), (4) Date: Oct. 30, 2013

(87) PCT Pub. No.: WO2012/161717
PCT Pub. Date: Nov. 29, 2012

(65) Prior Publication Data
US 2014/0074463 A1    Mar. 13, 2014

(51) Int. Cl.
G10L 21/00    (2013.01)
G10L 19/00    (2013.01)
H04R 25/00    (2006.01)
A61N 1/05    (2006.01)
A61N 1/36    (2006.01)
H03G 3/20    (2006.01)

(52) U.S. Cl.
CPC .............. *H04R 25/50* (2013.01); *A61N 1/0541* (2013.01); *A61N 1/36032* (2013.01); *H03G 3/20* (2013.01)

(58) Field of Classification Search
USPC ........................ 704/225, 228, 201, 200.1, 270
See application file for complete search history.

(56) References Cited

U.S. PATENT DOCUMENTS

| 5,396,562 | A | * | 3/1995 | Ishimitsu et al. | 381/107 |
| 5,640,450 | A | * | 6/1997 | Watanabe | 379/392 |
| 5,907,622 | A | * | 5/1999 | Dougherty | 381/57 |
| 5,983,183 | A | * | 11/1999 | Tabet et al. | 704/270 |

(Continued)

FOREIGN PATENT DOCUMENTS

| EP | 2164282 | 3/2010 |
| EP | 2205005 | 7/2010 |

OTHER PUBLICATIONS

Loizou, P.C., "Mimicking the human ear," Signal Processing Magazine, IEEE, vol. 15, No. 5, pp. 101,130, Sep. 1998.*

(Continued)

*Primary Examiner* — Edgar Guerra-Erazo
(74) *Attorney, Agent, or Firm* — ALG Intellectual Property, LLC (57) ABSTRACT

An exemplary system includes a detection facility configured to detect an input sound level of an audio signal presented to an auditory prosthesis patient; and an adaptive gain control (AGC) facility configured to 1) determine whether the detected input sound level is in a quiet region, an intermediate region, or a loud region, and 2) apply a gain to the audio signal in accordance with an AGC gain function that specifies the gain to be substantially equal to or less than a first gain threshold if the detected input sound level is in the quiet region, substantially equal to or less than a second gain threshold if the detected input sound level is in the loud region, and greater than the first and second gain thresholds if the detected input sound level is in the intermediate region. Corresponding systems and methods are also disclosed.

20 Claims, 11 Drawing Sheets

(56) References Cited

U.S. PATENT DOCUMENTS

| | | | |
|---|---|---|---|
| 6,805,633 B2* | 10/2004 | Hein et al. | 463/35 |
| 7,130,705 B2* | 10/2006 | Amir et al. | 700/94 |
| 7,366,315 B2 | 4/2008 | Blarney et al. | |
| 7,522,960 B2 | 4/2009 | Seligman | |
| 7,968,786 B2* | 6/2011 | Kemmochi et al. | 84/621 |
| 8,090,576 B2* | 1/2012 | Erell | 704/225 |
| 8,144,881 B2* | 3/2012 | Crockett et al. | 381/56 |
| 8,150,045 B2* | 4/2012 | Thuy et al. | 381/57 |
| 8,284,959 B2* | 10/2012 | Moon et al. | 381/106 |
| 8,422,706 B2* | 4/2013 | Kulkarni et al. | 381/317 |
| 8,428,270 B2* | 4/2013 | Crockett et al. | 381/56 |
| 8,437,482 B2* | 5/2013 | Seefeldt et al. | 381/104 |
| 8,538,749 B2* | 9/2013 | Visser et al. | 704/228 |
| 8,571,231 B2* | 10/2013 | Ramakrishnan et al. | 381/94.2 |
| 8,831,936 B2* | 9/2014 | Toman et al. | 704/228 |
| 8,849,433 B2* | 9/2014 | Seefeldt et al. | 700/94 |
| 9,049,524 B2* | 6/2015 | Griffin et al. | 1/1 |
| 2003/0023429 A1* | 1/2003 | Claesson et al. | 704/201 |
| 2007/0027676 A1* | 2/2007 | Chambers et al. | 704/200.1 |
| 2009/0299742 A1* | 12/2009 | Toman et al. | 704/233 |
| 2009/0304191 A1* | 12/2009 | Hoang Co Thuy et al. | 381/57 |
| 2010/0017205 A1* | 1/2010 | Visser et al. | 704/225 |
| 2010/0121635 A1* | 5/2010 | Erell | 704/225 |
| 2011/0064241 A1* | 3/2011 | Kulkarni et al. | 381/94.2 |
| 2011/0077712 A1 | 3/2011 | Killian | |
| 2011/0081026 A1* | 4/2011 | Ramakrishnan et al. | 381/94.3 |
| 2011/0098786 A1 | 4/2011 | Mishra et al. | |

OTHER PUBLICATIONS

Communication pursuant to Article 94(3) EPC received in European Patent Application No. 11723849.3, dated Oct. 9, 2014.

"Surgeon's Practice Kit", Instructions for Use (Part No. Z605502), *Cochlear Ltd (ABN 96 002 618 073)*, 14 Mars Road, Lane Cove NSW 2066, Australia, (2005).

International Search Report and Written Opinion received in International Application No. PCT/US11/038169 dated Apr. 27, 2012.

* cited by examiner

SYSTEMS AND METHODS FOR IMPROVING REPRESENTATION BY AN AUDITORY PROSTHESIS SYSTEM OF AUDIO SIGNALS HAVING INTERMEDIATE SOUND LEVELS

BACKGROUND INFORMATION

Auditory prosthesis patients (e.g., cochlear implant patients) often have trouble understanding relatively quiet sounds, such as soft speech. Traditional auditory prosthesis systems attempt to overcome this limitation by amplifying audio signals presented to auditory prosthesis patients before the signals are otherwise processed. However, in order to prevent already loud sounds from being further amplified, many auditory prosthesis systems use adaptive gain control ("AGC") to selectively amplify sounds below a predetermined input sound level (e.g., 60 dB SPL) and compress sounds above the predetermined input sound level.

Unfortunately, adaptive gain control also amplifies undesirable sounds, or noise, present below the predetermined input sound level. For example, environmental noise, system noise (e.g., microphone noise), and other types of noise are often present within the 20-40 dB SPL range, while soft speech is often within the 40-50 dB SPL range. In these situations, traditional adaptive gain control amplifies both the soft speech and the noise, thereby making it even more difficult, in some instances, for a patient to understand the soft speech.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for improving representation by an auditory prosthesis system of audio signals having intermediate sound levels are described herein. As will be described in more detail below, the systems and methods described herein may facilitate improved understanding by an auditory prosthesis patient of soft speech and other audio signals of interest (e.g., music, etc.) that fall within an intermediate input sound level range compared to low level noise and relatively loud sounds.

To this end, as will be described in more detail below, a speech processor communicatively coupled to an auditory prosthesis (e.g., a cochlear implant) that may be implanted within a patient may detect an input sound level of an audio signal presented to the patient. The speech processor may then determine whether the detected input sound level falls within a quiet region (i.e., a region that includes input sound levels at or below a first input sound level boundary), an intermediate region (i.e., a region that includes input sound levels above the first input sound level boundary and below a second input sound level boundary), or a loud region (e.g., a region that includes input sound levels at or above the second input sound level boundary). The speech processor may then apply a gain to the audio signal in accordance with an AGC gain function that specifies or sets the gain to be substantially equal to or less than a first gain threshold if the detected input sound level is in the quiet region, substantially equal to or less than a second gain threshold if the detected input sound level is in the loud region, and greater than the first and second gain thresholds if the detected input sound level is in the intermediate region.

To illustrate, the quiet region may be designated to include input sound levels at or below 30 dB SPL (a typical noise floor), the intermediate region may be designated to include input sound levels between 30 dB SPL and 60 dB SPL (a typical region in which soft speech may be present), and the loud region may be designated to include input sound levels at or above 60 dB SPL (a typical region of relatively loud sounds). With these designations in place, soft speech and other sounds that fall within the intermediate region may be amplified while the loudness level of audio signals that comprise noise and loud sounds may be either maintained or compressed. In this manner, an auditory prosthesis patient may more effectively perceive and/or understand soft speech.

In some examples, the AGC gain function used to apply gain to audio signals presented to an auditory prosthesis patient may be dynamically adjusted in response to one or more factors. For example, a speech processor may detect a noise level associated with an audio signal presented to an auditory prosthesis patient and dynamically adjust an AGC gain function in accordance with the detected noise level. The speech processor may then apply a gain to the audio signal in accordance with the adjusted AGC gain function.

To illustrate, a speech processor may detect an increase in noise that may result from an auditory prosthesis patient moving from one environment to another. In response, the sound processor may decrease a range of an expansion phase (described in detail below) included in the AGC gain function to account for the increase in noise. In this manner, as will be described in more detail below, the speech processor may prevent the increased noise from being amplified along with the audio signal of interest.

Figure 1:
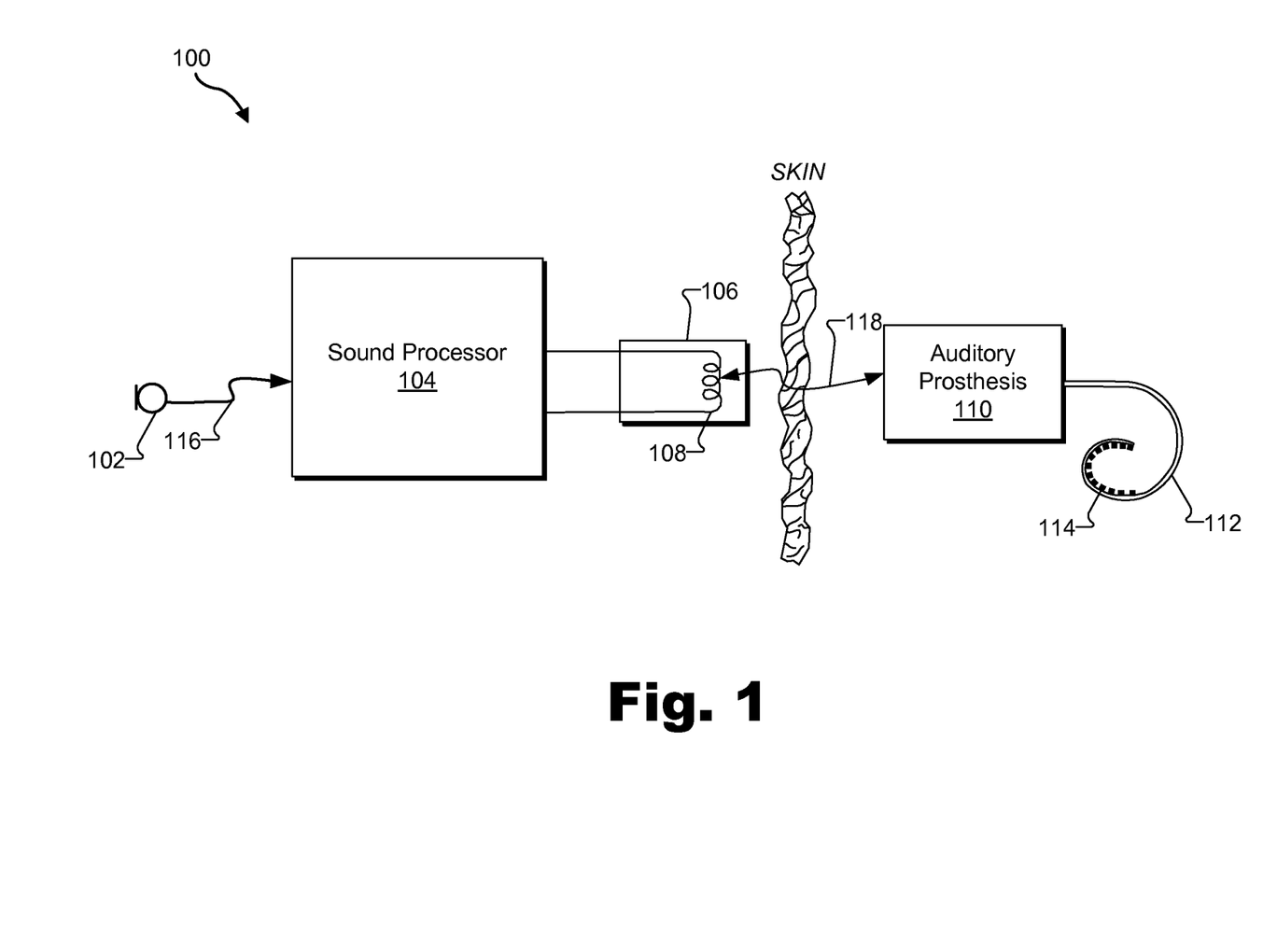
FIG. 1 illustrates an exemplary auditory prosthesis system according to principles described herein.

FIG. 1 illustrates an exemplary auditory prosthesis system 100. Auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the audio signal detected by microphone 102 in accordance with a selected sound processing strategy to generate appropriate stimulation parameters for controlling auditory prosthesis 110.

Sound processor 104 may be further configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

Sound processor 104 may include or be implemented by a behind-the-ear ("BTE") unit, a body-worn portable speech processor ("PSP"), and/or any other sound processing unit as may serve a particular implementation. Exemplary components of sound processor 104 will be described in more detail below.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

Figure 2:
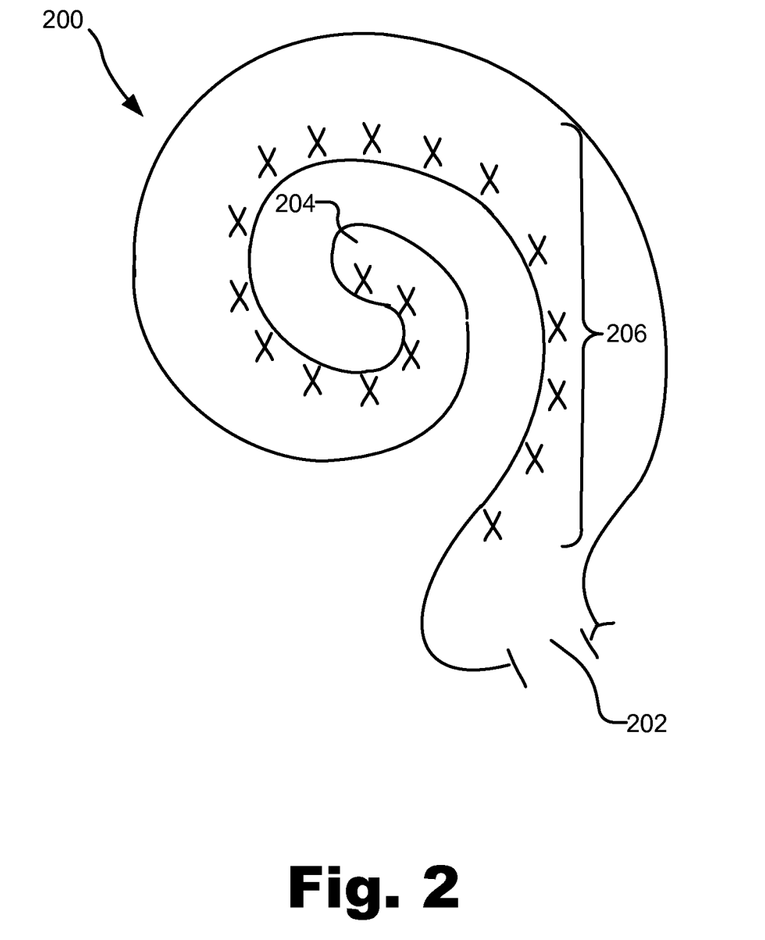
FIG. 2 illustrates a schematic structure of the human cochlea.

To facilitate application of the electrical stimulation generated by auditory prosthesis 110, lead 112 may be inserted within a duct of the cochlea such that electrodes 114 are in communication with one or more stimulation sites within the cochlea. FIG. 2 illustrates a schematic structure of the human cochlea 200 into which lead 112 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Auditory prosthesis system 100 may therefore be configured to apply electrical stimulation to different locations within the cochlea 200 (e.g., different locations along the auditory nerve tissue 206) to provide a sensation of hearing.

Alternatively, lead 112 may be implanted within a patient such that electrodes 114 are in communication with one or more stimulation sites otherwise located along the auditory pathway. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 3:
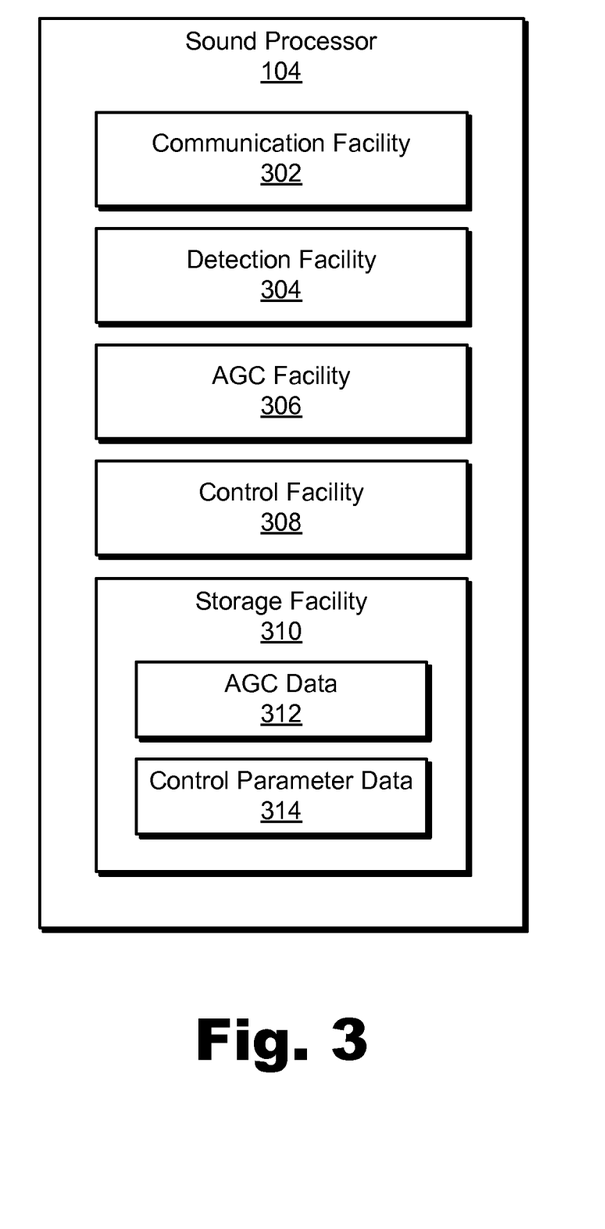
FIG. 3 illustrates exemplary components of a sound processor according to principles described herein.

FIG. 3 illustrates exemplary components of sound processor 104. As shown in FIG. 3, sound processor 104 may include a communication facility 302, a detection facility 304, an AGC facility 306, a control facility 308, and a storage facility 310, which may be in communication with one another using any suitable communication technologies. Each of these facilities 302-310 may include any combination of hardware, software, and/or firmware as may serve a particular implementation. For example, one or more of facilities 302-310 may include at least one computing device or processor configured to perform one or more of the functions described herein. Facilities 302-310 will now be described in more detail.

Communication facility 302 may be configured to facilitate communication between sound processor 104 and auditory prosthesis 110. For example, communication facility 302 may include transceiver components configured to wirelessly transmit data (e.g., control parameters and/or power signals) to auditory prosthesis 110 and/or wirelessly receive data from auditory prosthesis 110.

Detection facility 304 may be configured to detect an audio signal presented to an auditory prosthesis patient and one or more attributes associated therewith. For example, detection facility 304 may detect an input sound level of an audio signal presented to an auditory prosthesis patient. The input sound level of an audio signal may be represented in dB SPL, for example, and may be detected in any suitable manner.

Additionally or alternatively, detection facility 304 may detect a noise level associated with an audio signal presented to an auditory prosthesis patient. Detection facility 304 may detect the noise level using any suitable noise detection heuristic.

In some examples, detection facility 304 may detect a noise level associated with an audio signal by detecting a noise level of a noise signal presented to the auditory prosthesis patient concurrently with the audio signal. The noise signal may include ambient noise generated from the environment in which the patient is located, bodily noises (e.g., the patient's heartbeat), noise generated by any component of auditory prosthesis system 100, and/or any other type of noise as may serve a particular implementation. It will be recognized that, in some instances, detection facility 304 may detect a single composite signal comprising both the audio signal and the noise signal (e.g., a signal comprising a speech component and a noise component). Detection facility 304 may be configured to process the composite signal and separate out the noise signal (e.g., the noise component) and the audio signal of interest (e.g., the speech component) in accordance with any suitable noise detection heuristic as may serve a particular implementation.

Alternatively, detection facility 304 may detect a noise level associated with an audio signal by detecting an environment in which the auditory prosthesis patient is located and setting the noise level to be equal to a predetermined noise level associated with the detected environment. To illustrate, typical noise levels may be assigned to various environments in which the patient may be located. For example, a noise level of 30 dB SPL may be assigned to a quiet office in which the patient may located, a noise level of 60 dB SPL may be assigned to an outdoor environment in which the patient may be located, and a noise level of 70 dB SPL may be assigned to a relatively noisy restaurant in which the patient may be located. Detection facility 304 may then detect that the user has entered one of these predetermined environments and automatically set the noise level to be equal to the noise level assigned to that environment.

AGC facility 306 may be configured to perform one or more AGC functions with respect to an audio signal detected by detection facility 304. For example, AGC facility 306 may determine a particular sound level region in which the input sound level of the detected audio signal is located and apply a gain to the detected audio signal in accordance with an AGC gain function. The AGC gain function may be configured to specify an amount of gain that is to be applied to an audio signal by AGC facility 306 for any given input sound level. Exemplary AGC gain functions will be described in more detail below.

AGC facility 306 may be further configured to apply a gain to a detected noise signal in accordance with the AGC gain function. For example, detection facility 304 may detect a noise signal associated with an audio signal of interest. The noise signal may be subjected to the same AGC gain function to which the audio signal of interest is subjected. As will be described below, the AGC gain function may specify that a lower gain is to be applied to the noise signal than to the audio signal of interest.

In some examples, the AGC gain function used by AGC facility 306 may be adjusted, modified, or otherwise set by a user and/or automatically in response to one or more factors. For example, AGC facility 306 may adjust the AGC gain function in response to a change in a detected noise level associated with one or more audio signals presented to a patient. Examples of adjusting an AGC gain function will be described in more detail below.

Control facility 308 may be configured to perform one or more operations associated with a control of auditory prosthesis 110. For example, control facility may be configured to direct auditory prosthesis 110 to apply electrical stimulation (e.g., to one or more stimulation sites located within an auditory prosthesis patient) representative of an audio signal detected by detection facility 304 and subjected to adaptive gain control by AGC facility 306. To this end, control facility 308 may be configured to generate and transmit one or more control parameters (e.g., stimulation parameters) to auditory prosthesis 110.

Storage facility 310 may be configured to maintain AGC data 312 associated with and/or used by AGC facility 306 and control parameter data 314 representative of one or more control parameters, which may include one or more stimulation parameters (e.g., current steering parameters) to be transmitted from sound processor 104 to auditory prosthesis 110. Storage facility 310 may be configured to maintain additional or alternative data as may serve a particular implementation.

Figure 4:
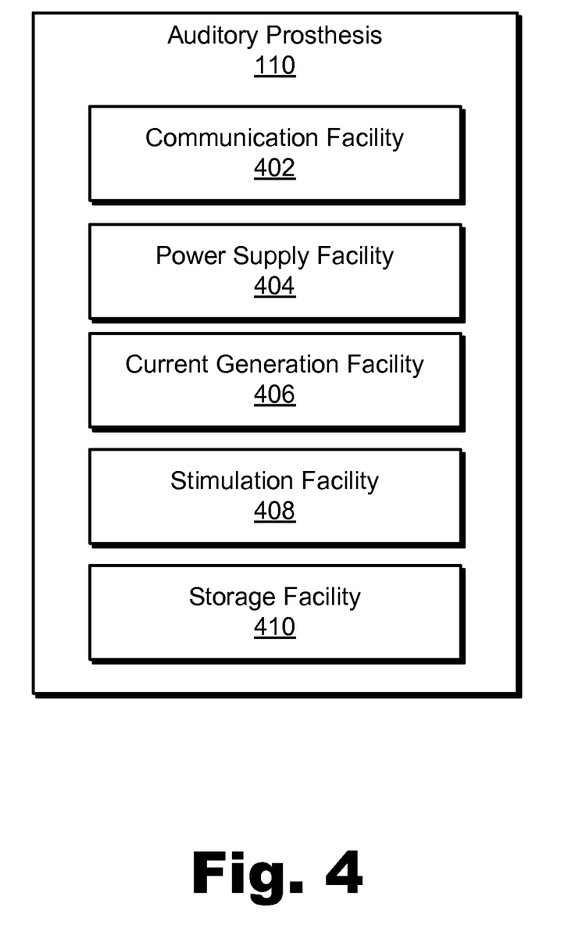
FIG. 4 illustrates exemplary components of an auditory prosthesis according to principles described herein.

FIG. 4 illustrates exemplary components of auditory prosthesis 110. As shown in FIG. 4, auditory prosthesis 110 may include a communication facility 402, a power supply facility 404, a current generation facility 406, a stimulation facility 408, and a storage facility 410, which may be in communication with one another using any suitable communication technologies. Each of these facilities 402-410 may include any combination of hardware, software, and/or firmware as may serve a particular application. For example, one or more of facilities 402-410 may include a computing device or processor configured to perform one or more of the functions described herein. Facilities 402-410 will now be described in more detail.

Communication facility 402 may be configured to facilitate communication between auditory prosthesis 110 and sound processor 104. For example, communication facility 402 may include one or more coils configured to receive control signals and/or power signals from sound processor 104. Communication facility 402 may additionally or alternatively be configured to transmit one or more status signals and/or other data to sound processor 104.

Power supply facility 404 may be configured to provide power to various components included within auditory prosthesis 110. To this end, power supply facility 404 may be configured to derive a compliance voltage from a power signal received from sound processor 104. The compliance voltage may be used by current generation facility 404 to generate stimulation current and/or by any other component within auditory prosthesis 110.

Current generation facility 406 may be configured to generate stimulation current in accordance with one or more stimulation parameters received from sound processor 104.

To this end, current generation facility 406 may include one or more current generators and/or any other circuitry configured to facilitate generation of stimulation current. For example, current generation facility 406 may include an array of independent current generators each corresponding to a distinct electrode or channel.

Stimulation facility 408 may be configured to facilitate application of the stimulation current generated by current generation facility 406 to one or more stimulation sites within the patient in accordance with one or more stimulation parameters received from sound processor 104.

Storage facility 410 may be configured to maintain data generated and/or utilized by auditory prosthesis 110. For example, storage facility 410 may maintain data representative of one or more stimulation parameters configured to define the stimulation current generated and applied by auditory prosthesis 110.

Figure 5:
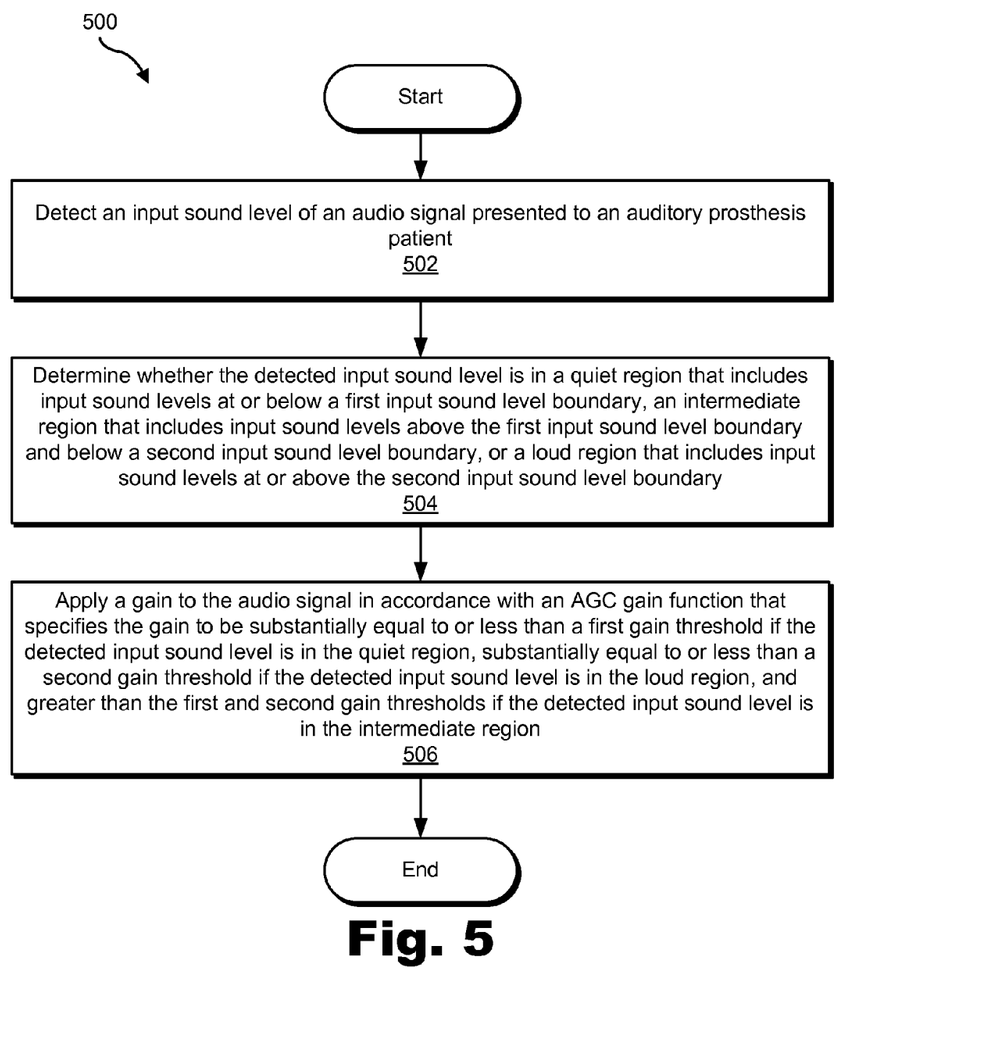
FIG. 5 illustrates an exemplary method of improving representation by an auditory prosthesis system of audio signals having intermediate sound levels according to principles described herein.

FIG. 5 illustrates an exemplary method 500 of improving representation by an auditory prosthesis system of audio signals having intermediate sound levels. While FIG. 5 illustrates exemplary steps according to one embodiment, other embodiments may omit, add to, reorder, and/or modify any of the steps shown in FIG. 5. One or more of the steps shown in FIG. 5 may be performed by any component or combination of components of sound processor 104.

In step 502, a sound processor detects an input sound level of an audio signal presented to an auditory prosthesis patient. The sound processor may detect the input sound level of the audio signal in any of the ways described herein.

In step 504, the sound processor determines whether the detected input sound level is in a quiet region that includes input sound levels at or below a first input sound level boundary, an intermediate region that includes input sound levels above the first input sound level boundary and below a second input sound level boundary, or a loud region that includes input sound levels at or above the second input sound level boundary. The sound processor may determine which sound level region within which the detecting input sound level falls in any of the ways described herein.

In step 506, the sound processor applies a gain to the audio signal in accordance with an AGC gain function that specifies the gain to be substantially equal to or less than a first gain threshold if the detected input sound level is in the quiet region, substantially equal to or less than a second gain threshold if the detected input sound level is in the loud region, and greater than the first and second gain thresholds if the detected input sound level is in the intermediate region. The sound processor may apply a gain to the audio signal in any of the ways described herein.

An exemplary implementation of method 500 by sound processor 104 will now be described. It will be recognized that the exemplary implementation that will be described is merely illustrative of the many different possible implementations of method 500.

Figure 6:
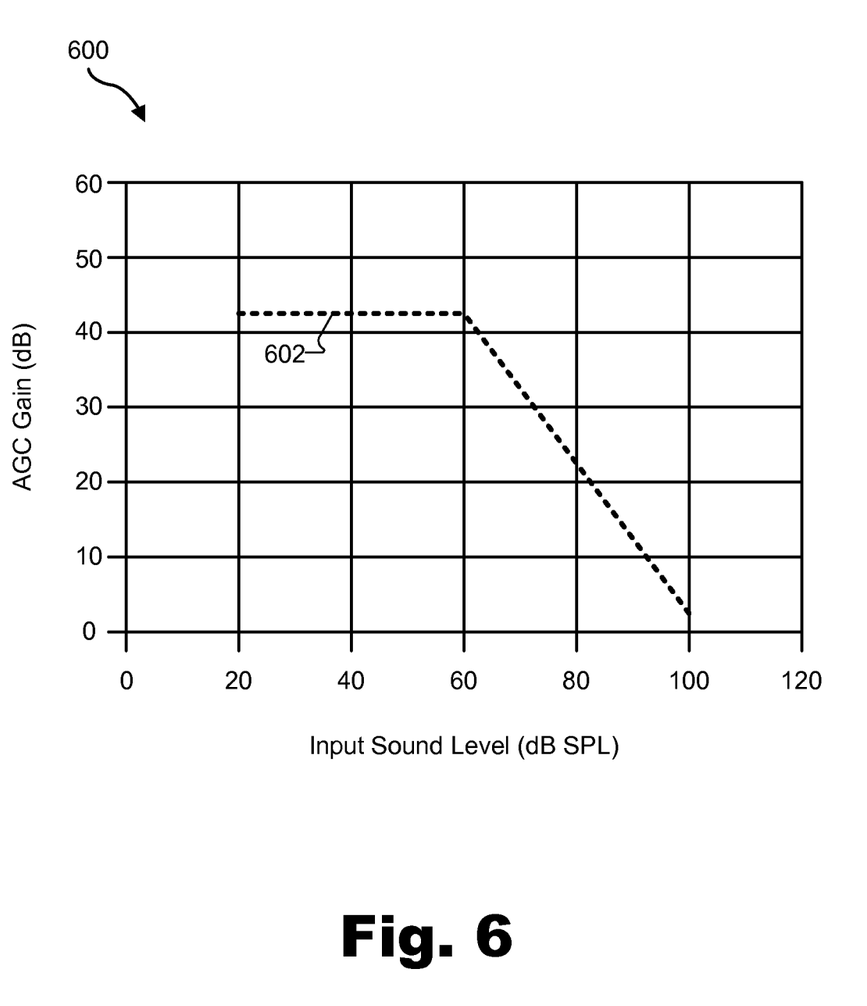
FIGS. 6-8 show various exemplary AGC gain functions according to principles described herein.

FIG. 6 shows a graph 600 illustrating an exemplary AGC gain function 602 that may be used by some sound processors to determine a gain to apply to an audio signal presented to an auditory prosthesis patient. As shown, AGC gain function 602 defines a mapping between possible input sound levels (in dB SPL) of an audio signal and corresponding gains (in dB) that may be applied to the audio signal. For example, AGC gain function 602 specifies that a gain of approximately 42 dB may be applied to audio signals having input sound levels of 20 to 60 dB SPL. However, for input sound levels greater than 60 dB SPL, AGC gain function 602 specifies that a sound processor will progressively apply less gain as the input sound level increases. In this manner, relatively loud sounds (which, in this case, include input sound levels above 60 dB SPL) are amplified less than relatively quiet sounds (which, in this case, include input sound levels below 60 dB SPL).

However, as described above, it may be disadvantageous to linearly apply the same amount of gain to all relatively quiet input sound levels (e.g., all input sound levels less than or equal to 60 dB SPL) as specified by AGC gain function 602. For example, an audio signal including soft speech may have an input sound level of 45 dB SPL. However, a noise level of noise associated with the audio signal may have an input sound level of approximately 30 dB SPL. In accordance with AGC gain function 602, an equal amount of gain will be applied to the soft speech and the noise. Such amplification of the noise may drown out the soft speech and make it difficult for the patient to understand the soft speech.

Figure 7:
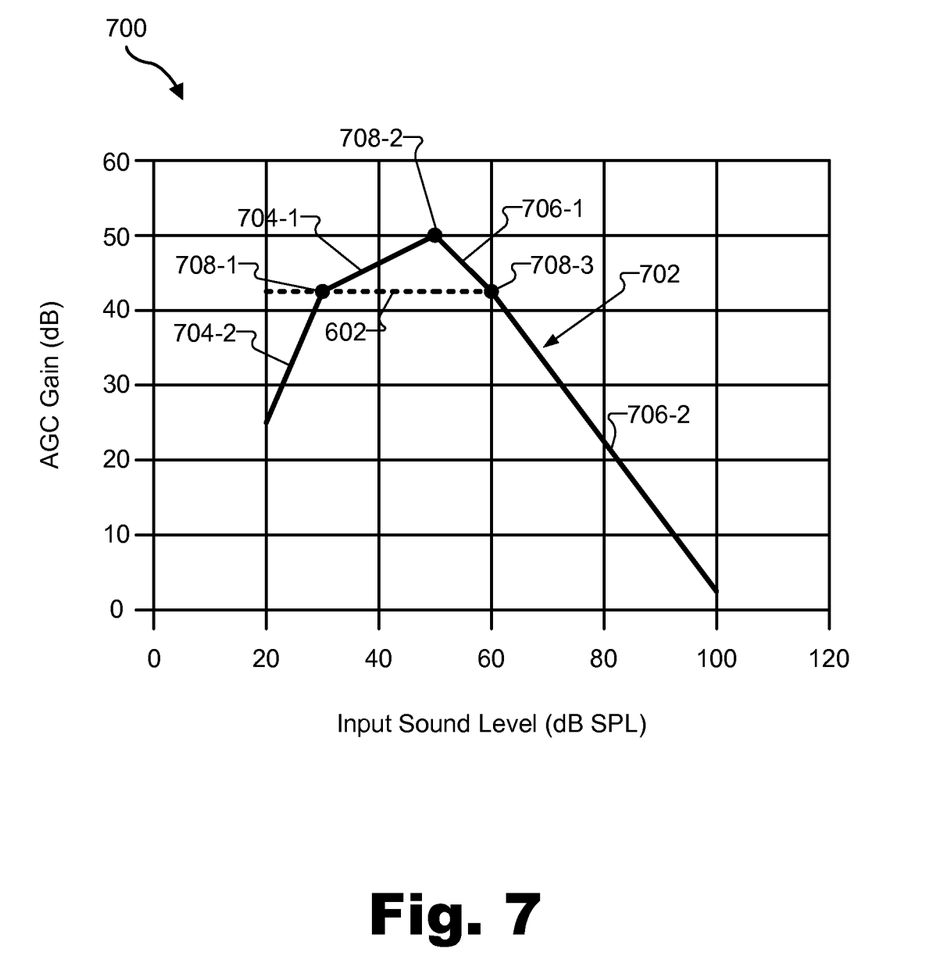

Hence, in accordance with the systems and methods described herein, an AGC gain function may be set to selectively amplify audio signals having intermediate sound levels more than audio signals having relatively low sound levels (i.e., low level noise) and audio signals having relatively high sound levels (i.e., loud sounds). For example, FIG. 7 shows a graph 700 illustrating an exemplary AGC gain function 702 configured to selectively amplify audio signals having intermediate sound levels more than audio signals having relatively low sound levels and audio signals having relatively high sound levels. AGC gain function 602 is also shown in FIG. 7 for comparative purposes.

As shown, AGC gain function 702 includes first and second expansion phases 704-1 and 704-2 (collectively referred to as "expansion phases 704") and first and second compression phases 706-1 and 706-2 (collectively referred to as "compression phases 706"). As used herein, an "expansion phase" refers to an input sound level range over which the slope of AGC gain function 702 is positive and a "compression phase" refers to an input sound level range over which the slope of AGC gain function 702 is negative. In the example of FIG. 7, first expansion phase 704-1 includes input sound levels in between 30 dB SPL and 50 dB SPL, second expansion phase 704-2 includes input sound levels below 30 dB SPL, first compression phase 706-1 includes input sound levels in between 50 dB SPL and 60 dB SPL, and second compression phase 706-2 includes input sound levels above 60 dB SPL.

The points within the graph at which the various expansion and compression phases intersect may be referred to as "knee points" 708 (e.g., low knee point 708-1, mid knee point 708-2, and high knee point 708-3). As will be described below, an AGC gain function (e.g., AGC gain function 702) may be adjusted or otherwise set by adjusting or otherwise specifying a position of knee points 708 within graph 700.

In some examples, the low and high knee points 708-1 and 708-3 may correspond to the input sound level boundaries that define the various sound level regions (e.g., the quiet, intermediate, and loud regions described herein) within which a detected input sound level may fall. To illustrate, in the example of FIG. 7, low knee point 708-1 corresponds to an input sound level boundary of 30 dB and high knee point 708-2 corresponds to an input sound level boundary of 60 dB. Hence, the quiet region includes input sound levels at or below 30 dB SPL, the intermediate region includes input sound levels between 30 dB SPL and 60 dB SPL, and the loud region includes input sound levels at or above 60 dB SPL. It will be recognized, however, that the low and high knee points 708-1 and 708-3 do not necessarily have to correspond to the input sound level boundaries. An example of this will be described below.

The low and high knee points 708-1 and 708-3 may also correspond to the various gain thresholds described herein. For example, low and high knee points 708-1 and 708-3 both correspond to a gain threshold of approximately 42 dB. Hence, in accordance with the systems and methods described herein, the gain applied to audio signals having input sound levels within the quiet region (i.e., at or below 30 dB SPL) is less than or equal to 42 dB. Likewise, the gain applied to audio signals having input sound levels within the loud region (i.e., at or above 60 dB SPL) is also less than or equal to 42 dB. However, the gain applied to audio signals having input sound levels that fall within the intermediate region (i.e., 30-60 dB SPL) is greater than 42 dB. It will be recognized, however, that the low and high knee points 708-1 and 708-3 do not necessarily have to correspond to the gain thresholds described herein. An example of this will be described below.

Compared to AGC gain function 602, AGC gain function 702 not only increases the amount of gain applied to sounds that fall within the intermediate region, but also compresses the sound level of sounds that fall within the quiet region. In this manner, soft speech and other audio signals of interest that fall within the intermediate region may be more readily understood by an auditory prosthesis patient.

Figure 8:
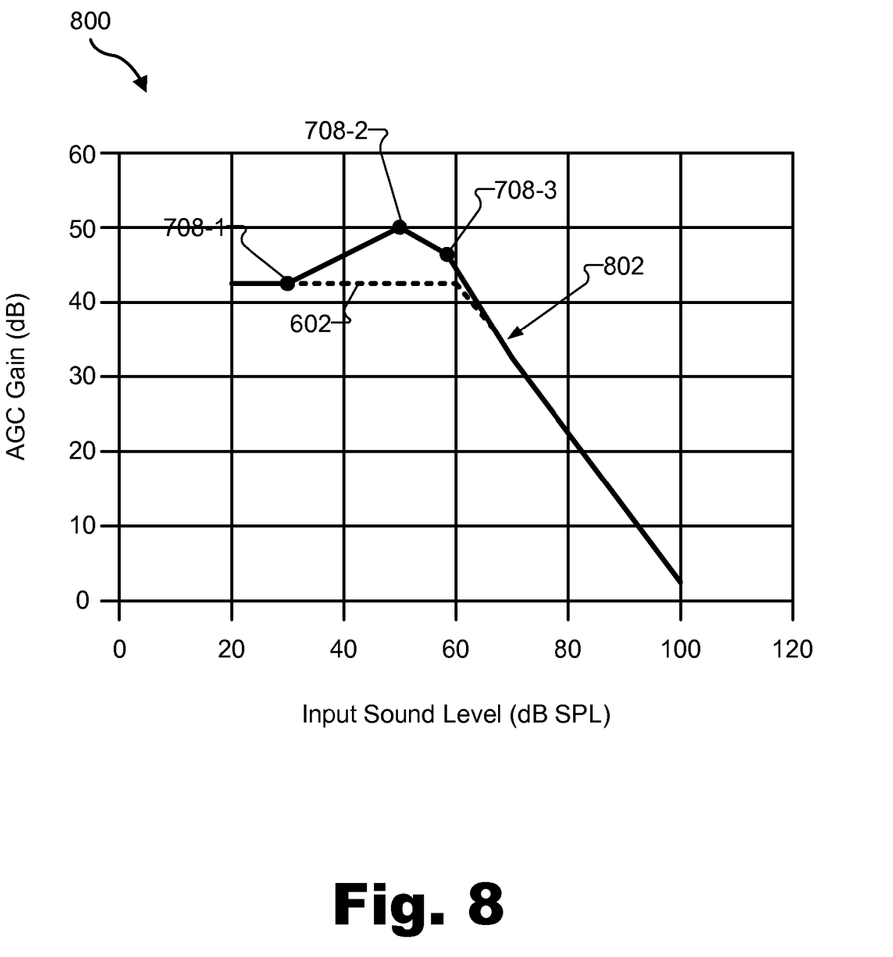

It will be recognized that AGC gain function 702 is merely illustrative of the many different AGC gain functions 702 that may be used in accordance with the systems and methods described herein. For example, FIG. 8 shows a graph 800 illustrating another exemplary AGC gain function 802 that may be used in accordance with the systems and methods described herein. AGC gain function 602 is also shown for comparative purposes.

As shown, AGC gain function 802 may not actually compress sounds included in the quiet region (i.e., sounds that have input sound levels at or below 30 dB). Rather, AGC gain function 802 may simply maintain a constant level of amplification for such sounds in a similar manner to that of AGC gain function 602. Another distinct feature of AGC gain function 802 is that high knee point 708-3 corresponds to a gain (i.e., a gain of approximately 47 dB) that is higher than the gain (i.e., a gain of approximately 42 dB) to which low knee point 708-1 corresponds.

In some examples, the input sound level boundaries that define the various sound level regions within FIG. 8 may still be 30 dB SPL and 60 dB SPL. In this case, the gain threshold corresponding to 30 dB SPL is approximately 42 dB and the gain threshold corresponding to 60 dB SPL is approximately 45 dB. Hence, this example illustrates an AGC gain function having a high knee point 708-3 that does not correspond to a sound level boundary or a gain threshold.

Figure 9:
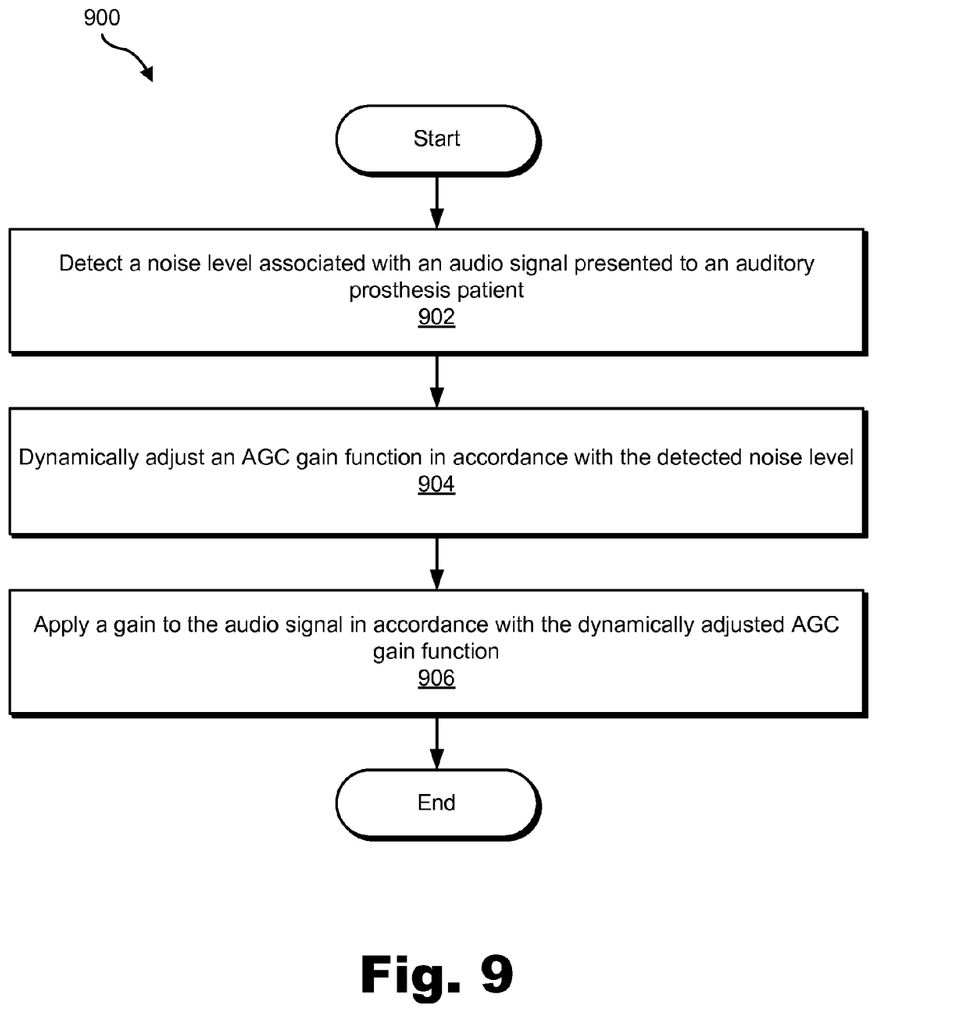
FIG. 9 illustrates another exemplary method of improving representation by an auditory prosthesis system of audio signals having intermediate sound levels according to principles described herein.

FIG. 9 illustrates another exemplary method 900 of improving representation by an auditory prosthesis system of audio signals having intermediate sound levels. While FIG. 9 illustrates exemplary steps according to one embodiment, other embodiments may omit, add to, reorder, and/or modify any of the steps shown in FIG. 9. One or more of the steps shown in FIG. 9 may be performed by any component or combination of components of sound processor 104.

In step 902, a sound processor detects a noise level associated with an audio signal presented to an auditory prosthesis patient. The sound processor may detect the noise level in any of the ways described herein.

In step 904, the sound processor dynamically adjusts an AGC gain function in accordance with the detected noise level. The AGC gain function may be dynamically adjusted in any of the ways described herein.

In step 906, the sound processor applies a gain to the audio signal in accordance with the dynamically adjusted AGC gain function. The gain may be applied to the audio signal in any of the ways described herein.

An exemplary implementation of method 900 by sound processor 104 will now be described. It will be recognized that the exemplary implementation that will be described is merely illustrative of the many different possible implementations of method 900.

In some examples, an AGC gain function may be initially set to be equal to AGC gain function 702, as described above in connection with FIG. 7. One or more audio signals presented to an auditory prosthesis patient may be subjected to AGC gain function 702. Subsequently, sound processor 104 may detect a change in a noise level associated with the audio signals being presented to the auditory prosthesis patient. For example, sound processor 104 may detect that the user has moved from a relatively quiet environment to a relatively loud environment and that the noise floor has increased from approximately 30 dB SPL to 40 dB SPL. In response to the increased noise level, sound processor 104 may dynamically adjust AGC gain function 702 by adjusting one or more characteristics of AGC gain function 702. For example, sound processor 104 may dynamically adjust AGC gain function 702 to account for the increased noise level by decreasing a range of expansion phase 704-1.

Figure 10:
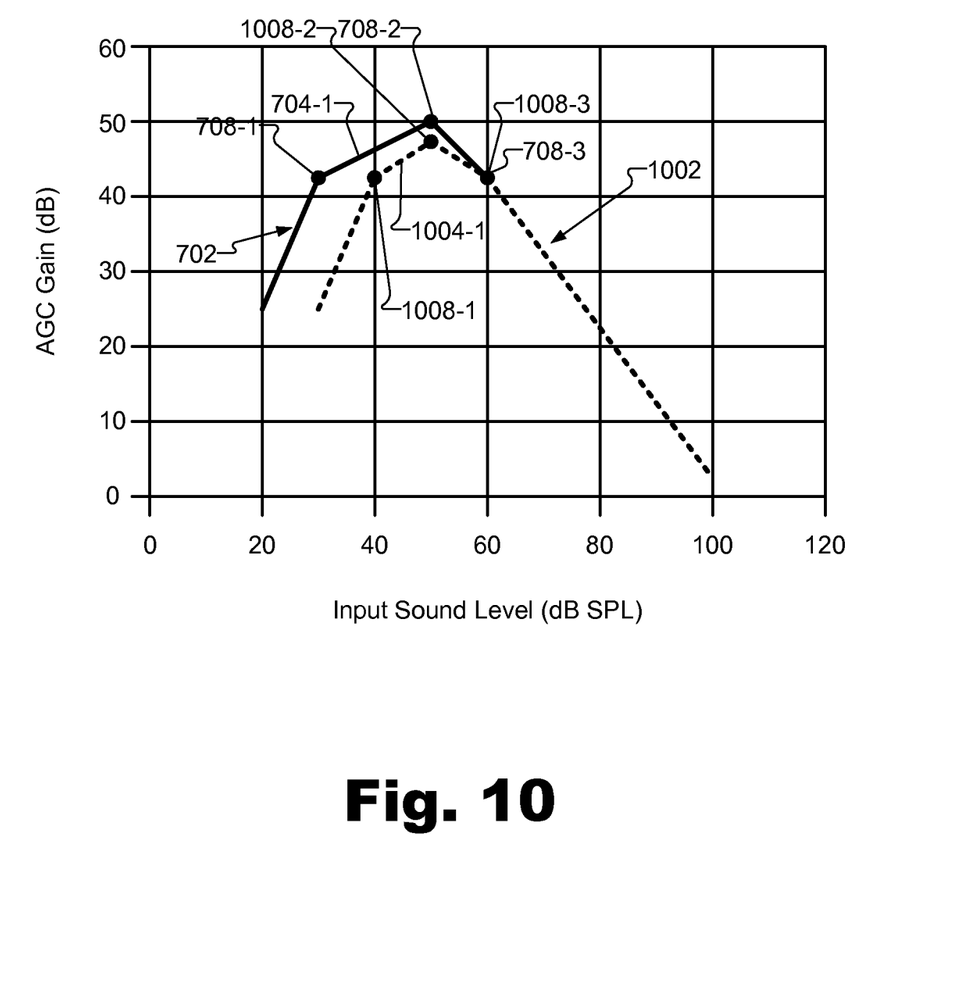
FIG. 10 shows an adjusted AGC gain function that may be derived by decreasing a range of an expansion phase according to principles described herein.

To illustrate, FIG. 10 shows an adjusted AGC gain function 1002 that may be derived by decreasing a range of expansion phase 704-1 of AGC gain function 702 (also illustrated in FIG. 10 for comparative purposes). As shown, adjusted AGC gain function 1002 includes an expansion phase 1004-1 that has a decreased range with respect to expansion phase 704-1 of AGC gain function 702. Expansion phase 704-1 may be adjusted by repositioning one or more knee points of AGC gain function 702 and/or in any other manner as may serve a particular implementation. For example, FIG. 10 shows that an input sound level positioning of low knee point 708-1 has been increased from 30 dB SPL to 40 dB SPL (as illustrated by low knee point 1008-1). FIG. 10 also shows that a gain positioning of mid knee point 708-2 has been decreased from 50 dB to approximately 47 dB (as illustrated by mid knee point 1008-2). Mid knee point 708-2 may be adjusted in this manner in order to keep a slope of expansion phase 1004-1 within a predetermined limit. High knee point 708-3 has not been adjusted, as illustrated by high knee point 1008-3.

Adjusting AGC gain function 702 in the manner illustrated in FIG. 10 may prevent the increased noise level from being amplified as much as audio signals of interest within the intermediate region. In this manner, the auditory prosthesis patient may more easily understand soft speech and other intermediate sound level sounds.

Alternatively, sound processor 104 may detect a change in a noise level associated with the audio signals being presented to the auditory prosthesis patient. For example, sound processor 104 may detect that the user has moved from an environment having a noise floor of 30 dB SPL to an environment having a noise floor of 25 dB SPL. In response to the decreased noise level, sound processor 104 may dynamically adjust AGC gain function 702 by adjusting one or more characteristics of AGC gain function 702. For example, sound processor 104 may dynamically adjust AGC gain function 702 to account for the decreased noise level by decreasing a range of expansion phase 704-1.

Figure 11:
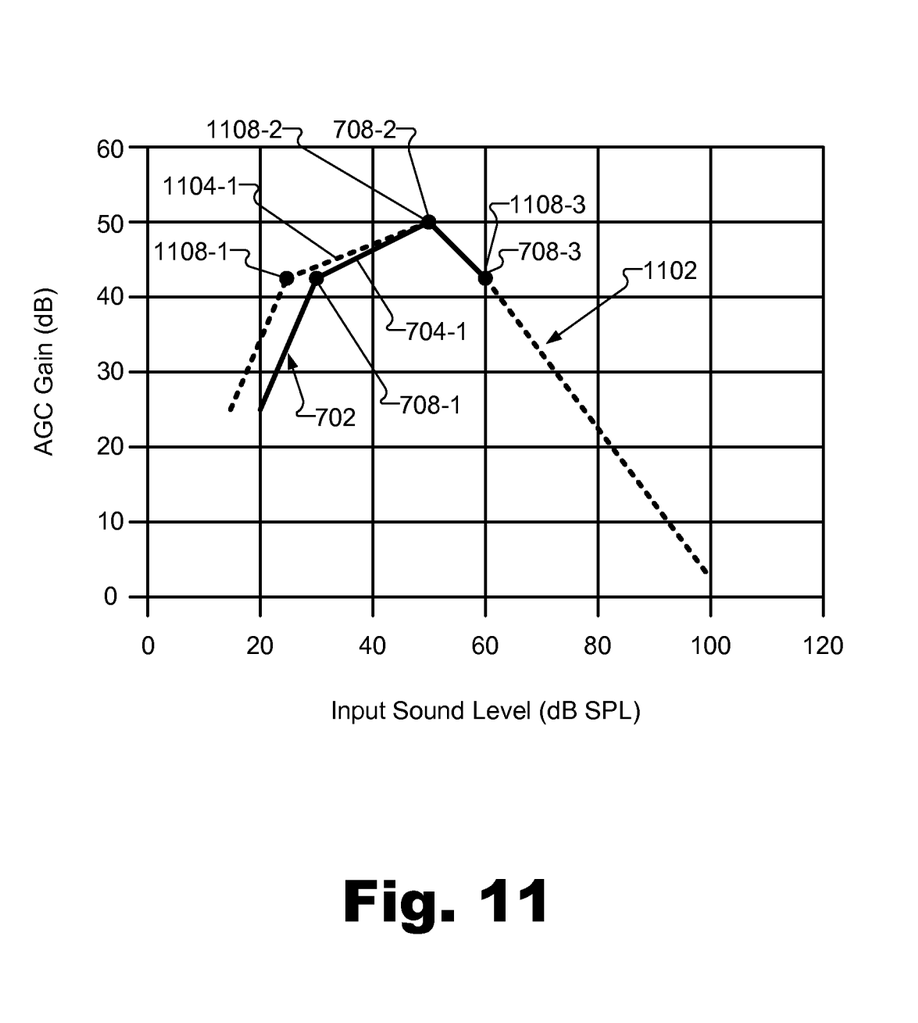
FIG. 11 shows an adjusted AGC gain function that may be derived by increasing a range of an expansion phase according to principles described herein.

To illustrate, FIG. 11 shows an adjusted AGC gain function 1102 that may be derived by increasing a range of expansion phase 704-1 of AGC gain function 702 (also illustrated in FIG. 11 for comparative purposes). As shown, adjusted AGC gain function 1102 includes an expansion phase 1104-1 that has an increased range with respect to expansion phase 704-1 of AGC gain function 702. Expansion phase 704-1 may be adjusted by repositioning one or more knee points of AGC gain function 702 and/or in any other manner as may serve a particular implementation. For example, FIG. 11 shows that an input sound level positioning of low knee point 708-1 has been decreased from 30 dB SPL to approximately 25 dB SPL (as illustrated by adjusted low knee point 1108-1). Knee points 708-2 and 708-3 remain unchanged, as illustrated by knee points 1108-2 and 1108-3. Adjusting AGC gain function 702 in the manner illustrated in FIG. 11 may facilitate increased understanding of especially low sound level audio signals of interest.

It will be recognized that the adjustments of AGC gain function 702 as illustrated in FIGS. 10-11 may be subject to compliance with predetermined signal-to-noise ratio thresholds, one or more noise characteristics, and/or any other limitation as may serve a particular implementation.

Sound processor 104 (i.e., AGC facility 306) may be configured to transition between applying different gains to different incoming audio signals in accordance with a syllabic compressor heuristic, a slow compressor heuristic, or a dual loop compressor heuristic (i.e., a combination of syllabic and slow compressor heuristics) as may serve a particular implementation. Syllabic compression follows the syllabic rate (e.g., 4 Hz). Slow compression is relatively slower (e.g., at the sentence level). In some examples, sound processor 104 may use the syllabic compressor heuristic for sound levels that fall within an expansion range of an AGC gain function and the dual loop compressor heuristic for sound levels that fall within a compression range of an AGC gain function.

In some examples, an AGC gain function may be specific to a particular channel or subset of channels included in a plurality of channels associated with auditory prosthesis 110. In such instances, one or more other channels included in the plurality of channels may each be associated with a different AGC gain function than the AGC gain function specific to the particular channel. For example, a first AGC gain function may be associated with a first subset of channels included in a plurality of channels associated with auditory prosthesis 110 and a second AGC gain function may be associated with a second subset of channels included in the plurality of channels.

Alternatively, the same AGC gain function may be used for each channel within a plurality of channels. For example, the same AGC gain function may be used for each channel included in a plurality of channels associated with a particular signal processing strategy or for a subset of channels included in the plurality of channels associated with the particular signal processing strategy.

In yet another alternative embodiment, multiple channels may be related or coupled one to another. For example, AGC facility 306 may average in (e.g., with lower weighting) or otherwise include input sound levels (i.e., energy) from channels adjacent to a particular channel when applying an AGC gain function to the input sound level of the particular channel. Additionally or alternatively, AGC facility 306 may not allow the gains in adjacent channels to be different by more than a predetermined threshold. In this manner, an auditory prosthesis patient may more effectively perceive and/or understand the sounds associated with the adjacent channels.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a detection facility that detects an input sound level of an audio signal presented to an auditory prosthesis patient; and
   an adaptive gain control ("AGC") facility communicatively coupled to the detection facility and that
      determines whether the detected input sound level is in a quiet region that includes input sound levels at or below a first input sound level boundary, an intermediate region that includes input sound levels above the first input sound level boundary and below a second input sound level boundary, or a loud region that includes input sound levels at or above the second input sound level boundary, and
      applies a gain to the audio signal in accordance with an AGC gain function that specifies the gain to be substantially equal to or less than a first gain threshold if the detected input sound level is in the quiet region, substantially equal to or less than a second gain threshold if the detected input sound level is in the loud region, and greater than the first and second gain thresholds if the detected input sound level is in the intermediate region.

2. The system of claim 1, wherein the application of the gain to the audio signal results in an amplified audio signal, and wherein the system further comprises a control facility communicatively coupled to the AGC facility and that directs an auditory prosthesis to apply electrical stimulation representative of the amplified audio signal.

3. The system of claim 1, wherein:
   the detection facility further
      detects an input sound level of an additional audio signal presented to the auditory prosthesis patient, and
      detects a noise level associated with the additional audio signal; and
   the AGC facility further
      dynamically adjusts the AGC gain function in accordance with the detected noise level, and
      applies a gain to the additional audio signal in accordance with the dynamically adjusted AGC gain function.

4. The system of claim 1, wherein the AGC gain function:
   defines a mapping between a plurality of input sound levels and a plurality of gains; and
   comprises an expansion phase within the intermediate region and a compression phase within the loud region.

5. The system of claim 4, wherein the expansion phase and the compression phase meet within the intermediate region.

6. The system of claim 4, wherein the AGC gain function further comprises an additional expansion phase within the quiet region.

7. The system of claim 4, wherein the AGC facility further uses a syllabic compressor heuristic during the expansion phase.

8. The system of claim 4, wherein the AGC facility further uses a dual loop heuristic during the compression phase.

9. The system of claim 1, wherein the AGC gain function is specific to a particular channel included in a plurality of channels associated with an auditory prosthesis communicatively coupled to the system, and wherein one or more other channels included in the plurality of channels are each associated with a different AGC gain function than the AGC gain function specific to the particular channel.

10. The system of claim 1, wherein the AGC gain function is associated with each channel included in a plurality of channels associated with an auditory prosthesis communicatively coupled to the system.

11. The system of claim 1, wherein the AGC gain function is associated with a first subset of channels included in a plurality of channels associated with an auditory prosthesis communicatively coupled to the system and another AGC gain function is associated with a second subset of channels included in the plurality of channels.

12. The system of claim 1, wherein the second gain threshold is greater than the first gain threshold.

13. A system comprising:
a detection facility that detects a noise level associated with an audio signal presented to an auditory prosthesis patient; and
an adaptive gain control ("AGC") facility communicatively coupled to the noise detection facility and that
dynamically adjusts an AGC gain function in accordance with the detected noise level, and
applies a gain to the audio signal in accordance with the dynamically adjusted AGC gain function.

14. The system of claim 13, wherein the noise level corresponds to a noise signal associated with the audio signal, and wherein the AGC facility further applies a gain to the noise signal in accordance with the dynamically adjusted AGC gain function.

15. The system of claim 13, wherein the detection facility detects the noise level associated with the audio signal by:
detecting an environment in which the auditory prosthesis patient is located; and
setting the noise level to be equal to a predetermined noise level associated with the detected environment.

16. The system of claim 13, wherein:
the detected noise level is higher than a previously detected noise level; and
the AGC facility dynamically adjusts the AGC gain function by decreasing a range of an expansion phase included in the AGC gain function.

17. The system of claim 13, wherein:
the detected noise level is lower than a previously detected noise level; and
the AGC facility dynamically adjusts the AGC gain function by increasing a range of an expansion phase included in the AGC gain function.

18. A method comprising:
detecting, by a speech processor, an input sound level of an audio signal presented to an auditory prosthesis patient;
determining, by the speech processor, whether the detected input sound level is in a quiet region that includes input sound levels at or below a first input sound level boundary, an intermediate region that includes input sound levels above the first input sound level boundary and below a second input sound level boundary, or a loud region that includes input sound levels at or above the second input sound level boundary; and
applying, by the speech processor, a gain to the audio signal in accordance with an adaptive gain control ("AGC") gain function that specifies the gain to be substantially equal to or less than a first gain threshold if the detected input sound level is in the quiet region, substantially equal to or less than a second gain threshold if the detected input sound level is in the loud region, and greater than the first and second gain thresholds if the detected input sound level is in the intermediate region.

19. The method of claim 18, wherein the applying of the gain to the audio signal results in an amplified audio signal, and wherein the method further comprises directing, by the speech processor, an auditory prosthesis to apply electrical stimulation representative of the amplified audio signal.

20. The method of claim 18, further comprising:
detecting, by the speech processor, an input sound level of an additional audio signal presented to the auditory prosthesis patient;
detecting, by the sound processor, a noise level associated with the additional audio signal;
dynamically adjusting, by the speech processor, the AGC gain function in accordance with the detected noise level; and
applying, by the speech processor, a gain to the additional audio signal in accordance with the dynamically adjusted AGC gain function.

* * * * *